(12) United States Patent
Day et al.

(10) Patent No.: US 6,379,648 B1
(45) Date of Patent: Apr. 30, 2002

(54) BIODEGRADABLE GLASS COMPOSITIONS AND METHODS FOR RADIATION THERAPY

(75) Inventors: Delbert E. Day, Rolla, MO (US); James E. White, Amherst, NY (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/241,892

(22) Filed: Feb. 1, 1999

(51) Int. Cl.[7] .......................... A61K 51/00; A61M 36/14
(52) U.S. Cl. ..................... 424/1.29; 424/1.37; 424/489; 424/490; 424/451; 424/457; 600/3; 501/33; 501/52; 252/644
(58) Field of Search .................................. 424/489, 490, 424/451, 457, 1.29, 1.37; 600/3; 501/33, 52; 252/644

(56) References Cited

U.S. PATENT DOCUMENTS

| | | | |
|---|---|---|---|
| 3,972,721 A | * | 8/1976 | Hammel et al. ............... 106/40 |
| 4,889,707 A | | 12/1989 | Day et al. ..................... 424/1.1 |
| 5,011,797 A | | 4/1991 | Day et al. ..................... 501/33 |
| 5,039,326 A | | 8/1991 | Day et al. .................... 65/21.1 |

OTHER PUBLICATIONS

Devi et al. "Optical Properties of $Pr^{3+}$ Ions in Lithium Borate Glasses" Physics and Chemistry of Glasses, vol. 37, No. 1 (1996) pp. 36–40.

Nachimuthu et al. "Influence of Cations on the Optical Properties of $Nd^{3+}$, $Eu^{3+}$ and $Er^{3+}$ Doped Borate Glasses" Physics and Chemistry of Glasses, vol. 38, No. 2 (1997) pp. 59–62.

International Search Report for analogous PCT Application No. PCT/US00/02388 dated Jun. 14, 2000.

* cited by examiner

Primary Examiner—Diana Dudash
Assistant Examiner—S Sharareh
(74) Attorney, Agent, or Firm—Senniger, Powers, Leavitt & Roedel

(57) ABSTRACT

A nonradioactive glass in particulate form adapted for radiation therapy in a mammal comprise a biodegradable rare earth-lithium borate glass material of a specified composition which, upon being subjected to an effective amount of neutron irradiation, will produce a beta or gamma emitting radioisotope, the radioisotope being distributed throughout the glass material, the glass upon being introduced into a body fluid for radiation therapy being adapted to react therewith causing the radioisotope to form an insoluble compound on the surface of the glass material which is retained in the glass material and thereby prevented from escaping from the treatment site. Radioactive glasses and methods for carrying out radiation therapy with such radioactive glasses are also disclosed.

11 Claims, 7 Drawing Sheets

BIODEGRADABLE GLASS COMPOSITIONS AND METHODS FOR RADIATION THERAPY

BACKGROUND OF THE INVENTION

This invention relates to radiation therapy such as radiation synovectomy of arthritic joints and biodegradable glass compositions in particulate form for use in radiation therapy.

Currently, no material for the in vivo delivery of therapeutic doses of beta radiation have been approved for use in the United States for irradiation of diseased organs in the body, e.g. malignant tumors and the inflamed synovium of arthritic joints. Materials that have been investigated previously for in vivo radiotherapy can be classified as bio-inert (non-degradable) glasses (e.g. Ehrhardt et al. Nuc. Med. Biol., 14 [3] (1987); Ehrhardt et al., Soc. of Nuc. Med., 39th Annual Meeting, June 9–12 (1992); Day et al., Advanced Series in Ceramics—Vol. 1, p. 305–317, World Scientific (1994); Hyatt et al., J. Am. Ceram. Soc., 70 [10] (1987); and Erbe et al., J. Biomed. Mat. Res., 27, 1301–1308 (1993)) or non-glasses (e.g. Ansell, Ann. Rheum. Dis., 6 Supp. 1–2 (1993); Ingrand, Ann. Rheum. Dis., 6 Supp. 3–9 (1973); Boerbooms et al., Eur. J. Nuc. Med., 10 (1985); Spooren et al., Eur. J. Nuc. Med., 10 (1985); and Neves et al., Appl. Rad. Isat., 38 [9] (1987)). All of these materials can be administered to the patient by injection in a similar fashion.

Bio-inert radiotherapy glass particulates have already demonstrated the effectiveness of glass materials for safely delivering large localized does of therapeutic beta radiation. However, such glasses are limited to therapies where the glass can remain in the body indefinitely. Radiation synovectomy of diseased joints is one example of an application where the eventual removal (clearance) of the radiopharmaceutical may be desired. This creates the need for a biodegradable material.

Non-glass materials that have been proposed for use as radiopharmaceuticals include radiocolloids and ceramic, polymer or protein particulates that have a radioactive isotope attached (bonded) to their surface. Several of these non-glass materials can be cleared from in vivo treatment sites such as a rheumatoid arthritic joint. Each has shortcomings, however, that limits their usefulness and safety during preparation and use. These shortcomings include: (1) release of excessive or potentially dangerous amounts of radiation outside the treatment site. This unwanted release has occurred due to the physical escape of the intact radioactive materials, the disintegration of the materials into smaller particles or ionic species while still radioactive, or the "debonding" of the radioisotope from the surface of a particle when in contact with body fluids; (2) the radiation dose is limited to amounts smaller than desired for certain applications; (3) complex preparation procedures that include handling radioactive substances during fabrication; and (4) use of radioisotopes with a short half life, which means that the material must be used quickly. This limits the time available for distributing (mailing) the radiopharmaceutical and causes other inconveniences.

Beta-emitting radionuclides are considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme; they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated.

It is fortuitous that beta emitters, the most useful radiotherapeutic radionuclides, are also the ones most copiously produced by neutron capture in nuclear reactors, the most powerful sources of radioisotopes. Reactor-produced isotopes number in the thousands, giving researchers a wide choice of isotopes of various half-lives, beta energies, gamma emissions, and chemical properties. Gamma emissions, while not as useful as beta emissions, play an important role in that they permit the distribution of radioisotope in the body to be observed using an Anger gamma ray camera or single photon computed tomography (SPECT) instrument. This permits direct observation and, to some extent, quantification of radionuclide leakage from an organ or a joint and also provides positive verification of the potency of joint injection and distribution of the radionuclide in the research animal.

With respect to radiation synovectomy of arthritic joints, treatment of the different depths of diseased synovium in joints of disparate size, such as the finger joints and the knee, requires isotopes of different average beta range. It is important to achieve a "kill" of sufficient depth to be efficacious without causing significant necrosis of overlying normal tissues.

Rare earth containing glass microspheres have been considered for radiation synovectomy treatment of rheumatoid arthritic joints. The radioactive glass microspheres could be injected directly into the synovial sac and deliver enough radiation ($\geq 10,000$ rads (cGy)) to destroy the inflamed lining of the diseased synovial membrane. Radiocolloid particulates, e.g. $^{90}Y$ or $^{198}Au$ salts, are presently used in Europe for radiation synovectomy (e.g. Houle et al., Radiology 172 [3] 1989); Russel et al., Endocurietherapy/Hyperthermia Oncology, 4 [7] 171–186 (1988); Sledge et al., Arth. Rheum. 29 [2] 153–159 (1986); Davis et al., J. Nucl. Med., 30 [6] 1047–1055 (1989); Hall, Orthop. Clin. North Am., 6, 675–684 (1975); and Taylor et al., Ann. Rheum. Dis., 31, 159–161 (1972)), but have not been approved for use in the United States because of unacceptable amounts of radiation leakage during their use. The radiocolloids are known to easily escape the synovium due to their sub-micron size, and in certain instances 25% of the targeted radiation has been deposited in healthy tissue outside the joint. Glass microspheres for radiotherapy are much larger (>1 μm in diameter) than the radiocolloids and have the additional advantage of a carefully controlled size within a few microns.

U.S. Pat. No. 5,011,797 dated Apr. 30, 1991 discloses radioactive microspheres for radiation synovectomy of arthritic joints which comprise a biodegradable glass material and a beta radiation emitting radioisotope chemically dissolved in and distributed substantially uniformly throughout the glass material. The biodegradable glass material may be lithium silicate, lithium aluminosilicate, lithium aluminoborate, lithium germanate, lithium aluminogermanate, potassium silicate, potassium aluminosilicate, potassium aluminoborate, potassium germanate or potassium aluminogermanate and the beta radiation emitting radioisotope may be samarium-153, holmium-166, erbium-169, dysprosium-165, rhenium-186, rhenium-188 or yttrium-90. The patent also discloses non-biodegradable glass materials such as magnesium aluminosilicate and aluminosilicate glass materials which contain a beta radiation emitting radioisotope.

There is a continuing need for improved glass materials adapted for radiation therapy such as radiation synovectomy of arthritic joints.

SUMMARY OF THE INVENTION

Among the several objects of the invention may be noted the provision of novel biodegradable rare earth-lithium borate glass materials for use in radiation therapy; the provision of such glass materials containing beta or gamma emitting radioisotopes; the provision of such glass materials in the form of microspheres; the provision of such biodegradable glass materials which upon being introduced into a body fluid for radiation therapy are adapted to react therewith causing the radioisotope contained therein to react with the body fluid causing the radioisotope to form an insoluble compound on the surface of the glass material which is retained on the glass material and thereby prevented from escaping from the treatment site; and the provision of methods for carrying out radiation therapy such as radiation synovectomy of arthritic joints. Other objects and features will be in part apparent and in part pointed out hereinafter.

Briefly, the present invention is directed to novel radioactive glass in particulate form for radiation therapy in a mammal comprising a biodegradable glass material having one of the following compositions:

$x\text{RE}_2\text{O}_3.(100-x)\text{LiB}_3\text{O}_5$, $x\text{RE}_2\text{O}_3.y\text{Li}_2\text{O}.(100-x-y)\text{B}_2\text{O}_3$, $x\text{RE}_2\text{O}_3.y\text{MgO}.(100-x-y)\text{LiB}_3\text{O}_5$, $x\text{RE}_2\text{O}_3.y\text{MgO}.(100-x-y)\text{Li}_2\text{B}_8\text{O}_{13}$, and $x\text{RE}_2\text{O}_3.3\text{MgO}.5\text{SiO}_2.y\text{Al}_2\text{O}_3.(92-y-x)\text{Li}_2\text{B}_8\text{O}_{13}$ wherein RE is a neutron activatable rare earth which emits a therapeutic intensity of beta or gamma radiation, the radioisotope being distributed throughout the glass material, x is the mole percent of $\text{RE}_2\text{O}_3$ and ranges between approximately 0.5 and 5 and y is the mole percent of $\text{Li}_2\text{O}$, MgO or $\text{Al}_2\text{O}_3$ and the balance is a lithium borate material glass. The lithium borate glass is substantially free of lithium-6 and boron-10 and the glass upon being introduced into a body fluid for radiation therapy is adapted to react therewith causing the radioisotope to form an insoluble compound on the surface of the glass material which is retained in the glass material and thereby prevented from escaping from the treatment site.

Another aspect of the invention resides in the provision of novel nonradioactive glass in particulate form which, upon being subjected to an effective amount of neutron irradiation, will produce a beta or gamma emitting radioisotope thereby rendering the glass material suitable for use for radiation therapy while avoiding the handling of radioactive elements during initial production of the glass material.

Still another aspect of the invention lies in the provision of novel methods for carrying out radiation therapy such as radiation synovectomy of arthritic joints utilizing the novel radioactive glass material of the invention.

DESCRIPTION OF THE PREFERRED EMBODIMENTS

Figure 1:
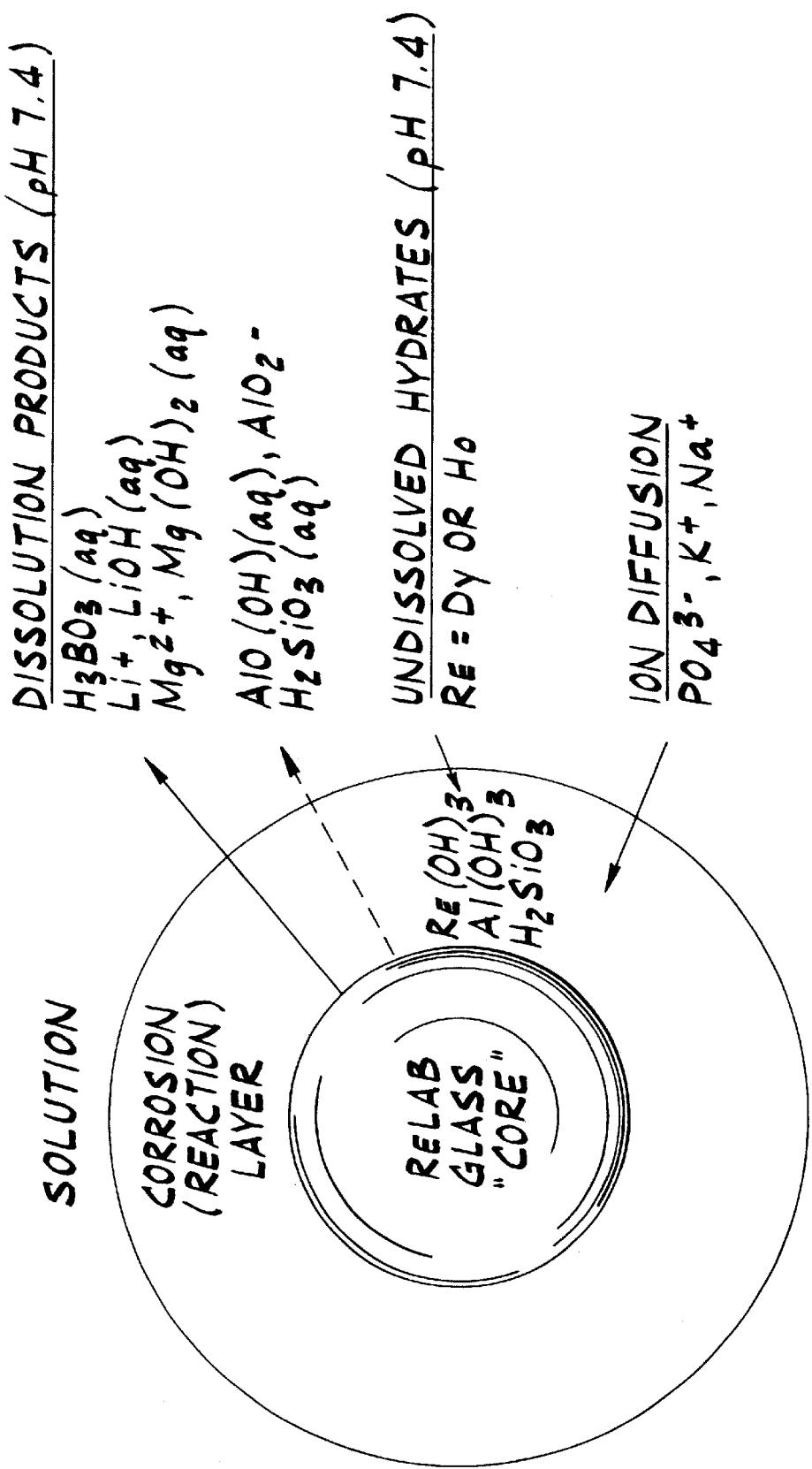
FIG. 1 is a schematic showing the formation of a corrosion (reaction) layer on the surface of rare earth-lithium borate glass microspheres as a result of non-uniform dissolution.

In accordance with the present invention, it has now been found that a certain class of novel radioactive glass materials in particulate form may be used for the in vivo irradiation of diseased organs in the body, e.g. malignant tumors and the inflamed synovium of arthritic joints. The glass materials may be in the form of microspheres which, upon being introduced into a body fluid for radiation therapy are adapted to have the beta or gamma emitting radioisotope contained therein react with the body fluid causing the radioisotope to form an insoluble compound on the surface of the glass material which is retained in the glass material and thereby prevented from escaping from the treatment site to other sites in the body. The radioactive glass materials of the invention are prepared from novel nonradioactive glass materials which may be manufactured, sized, and processed in other ways before radioactivity is induced providing the advantage of working only with nonradioactive materials during initial production of the glass materials.

In a first embodiment of the invention, the novel radioactive materials in particulate form (e.g. microspheres) are comprised of a biodegradable glass material having one of the following compositions:

$x\text{RE}_2\text{O}_3.(100-x)\text{LiB}_3\text{O}_5$ $x\text{RE}_2\text{O}_3.y\text{Li}_2\text{O}.(100-x-y)\text{B}_2\text{O}_3$ $x\text{RE}_2\text{O}_3.y\text{MgO}.(100-x-y)\text{LiB}_3\text{O}_5$

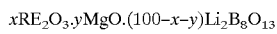

wherein RE is a neutron activatable rare earth radioisotope which emits a therapeutic intensity of beta or gamma radiation and is distributed throughout the glass material, x is the mole percent of $RE_2O_3$ and ranges between approximately 0.5 and 5, y is the mole percent of $Li_2O$, MgO or $Al_2O_3$ and the balance is a lithium borate glass material.

The lithium borate glass material is substantially free of lithium-6 and boron-10. Lithium-6 is a 7.4% naturally abundant isotope which forms tritium when naturally occurring lithium compounds are bombarded with neutrons. Tritium is a beta emitter with a half life of 12.5 years. Accordingly, compounds which contain just lithium-7 should be used since no radioactive isotopes are formed when lithium-7 is bombarded with neutrons. Boron-10 is an isotope with a large thermal cross section, 3837 barns, which would be detrimental in a glass material of the present invention because the glass might absorb so many neutrons as to prevent other portions of the glass from becoming radioactive. This problem can be avoided by using compounds which contain only boron-11 that has a much smaller thermal cross section, about 0.005 barns.

Any neutron activatable rare earth radioisotope which emits a therapeutic intensity of beta or gamma radiation may be used in the practice of the invention as a component of the above-noted glass material compositions. As used herein, the term neutron activatable rare earth radioisotope includes yttrium-90. Illustrative beta or gamma emitting radioisotopes include dysprosium-165, holmium-166, yttrium-90, rhenium-186, rhenium-188 and samarium-153. These beta or gamma emitting radioisotopes are particularly suitable for use in the present invention. Samarium-153 (46.3 hr. half-life) and holmium-166 (26.8 hr. half-life) can be readily dissolved in the above-noted glass compositions, have good activation properties in a nuclear reactor, possess imageable gamma rays, exhibit low toxicity and have half-lives long enough for distribution of the radioactive glass materials containing them.

Holmium-166 is produced by neutron capture on 100% abundant, stable holmium-165 with thermal neutron and resonance neutron cross sections of 61.2 and 67.0 barns, respectively. It decays with a 26.83 hour half-life by emission of 1.855 MeV (51%) and 1.776 MeV (48%) maximum energy beta particles with a maximum range of about 8.0 mm and an average range of about 2 mm. Since dysprosium-165 emits a beta particle of slightly lower maximum energy (1.31 MeV) and has proven efficacious in human knee radiation synovectomies, it appears that holmium-166 has sufficient penetration for this application. Ho-166 has sufficient penetration for this application. Ho-166 also emits an 80.5 Kev gamma ray in 6.2% abundance and thus is imageable by conventional techniques.

Samarium-153 is produced by neutron capture of natural or isotopically enriched samarium-152 with thermal and resonance neutron cross sections of 210 and 3,020 barns, respectively. it decays by beta emissions of 0.810 MeV (20%) 0.710 MeV (49%) and 0.640 MeV (30%) maximum energies with concomitant ranges of about 2.3 mm maximum and 0.8 mm average distance, respectively. Sm-153 has a physical half-life of 46.27 hours and produces a highly imageable 103 KeV gamma ray with an abundance of 29.8%, decaying to stable Eu-153.

Samarium-153 and holmium-166 are both chemically compatible and capable of being incorporated into the above-noted glass compositions in which no other significant radioactivities induced by neutron bombardment will be present after about one day of decay. Dysprosium-165, yttrium-90, rhenium-186 and rhenium-188 and other beta or gamma emitting radioisotopes may also be used as the radioisotope in the practice of the invention.

Illustrative of the biodegradable lithium borate glass materials within the above-noted compositions may be mentioned the following:

| | |
|---|---|
| $Dy_2O_3$ | 1.7 mole % |
| $Li_2O$ | 24.6 mole % |
| $B_2O_3$ | 73.7 mole % |
| | 100.0 mole % |
| $Dy_2O_3$ | 5 mole % |
| $Li_2O$ | 16 mole % |
| $Al_2O_3$ | 5 mole % |
| $B_2O_3$ | 66 mole % |
| $SiO_2$ | 5 mole % |
| MgO | 3 mole % |
| | 100 mole % |
| $Dy_2O_3$ | 5 mole % |
| $Li_2O$ | 15 mole % |
| $Al_2O_3$ | 10 mole % |
| $B_2O_3$ | 62 mole % |
| $SiO_2$ | 5 mole % |
| MgO | 3 mole % |
| | 100 mole % |
| $Ho_2O_3$ | 2 mole % |
| $Li_2O$ | 15 mole % |
| $Al_2O_3$ | 15 mole % |
| $B_2O_3$ | 60 mole % |
| $SiO_2$ | 5 mole % |
| MgO | 3 mole % |
| | 100 mole % |

It will be understood that other radioisotope-containing lithium borate glass materials within the above-noted compositions may also be used in the practice of the invention.

As previously indicated, the biodegradable rare earth-lithium borate glass materials of the invention corrode, react or biodegrade in the body at controlled rates determined by the specific glass composition. This biodegradation occurs in such a way that none of the beta or gamma emitting radioisotope contained in the glass escapes from the treatment site. Preferably, the glass materials are formed into microspheres of nearly any desired size, preferably microspheres having a diameter less than 100 microns and, more preferably, having a diameter between approximately 1 and 40 microns.

After administration to the treatment site for radiation therapy as by injection or other suitable conventional means known to the art, the radioactive rare earth element either reacts with another constituent in the glass or with a body fluid to form an insoluble compound on the surface of the glass material, which insoluble compound may eventually form throughout the glass material and be retained on the glass material and is thereby prevented from escaping from the treatment site. Referring to FIG. 1, there is shown a simplified model for the degradation or corrosion characteristics of dysprosium-165, holmium-166 or other rare earth lithium borate glass microspheres of the invention as employed for in vivo radiation therapy. FIG. 1 shows the presence of a corrosion or reaction layer on the surface of the glass microsphere due to the dissolution of the $B_2O_3$, $Li_2O$, MgO and, to a lesser extent, $Al_2O_3$ and $SiO_2$. The insoluble compound formed and retained on the glass material to prevent its unwanted migration to other sites may be, for example, a rare earth oxide, rare earth, hydroxide or rare earth phosphate. Some of the probable products of dissolution and undissolved $Dy_2O_3$ or $Ho_2O_3$, $Al_2O_3$ and $SiO_2$ are shown in FIG. 1. The diffusion of P, K and Na ions from body fluids into the corrosion or reaction layer of the glass microsphere is also indicated in FIG. 1. The undissolved oxides in the corrosion layer may become partially hydrated.

As shown by the experimental work set forth hereinafter, no measurable amount of radioactivity was released from neutron activated DyLAB glass microspheres after being immersed in deionized water at 37° C. for 11 hours. The lack of release of dysprosium-165 from the radioactive DyLAB microspheres was confirmed by similar measurements using non-radioactive microspheres.

Figure 5:
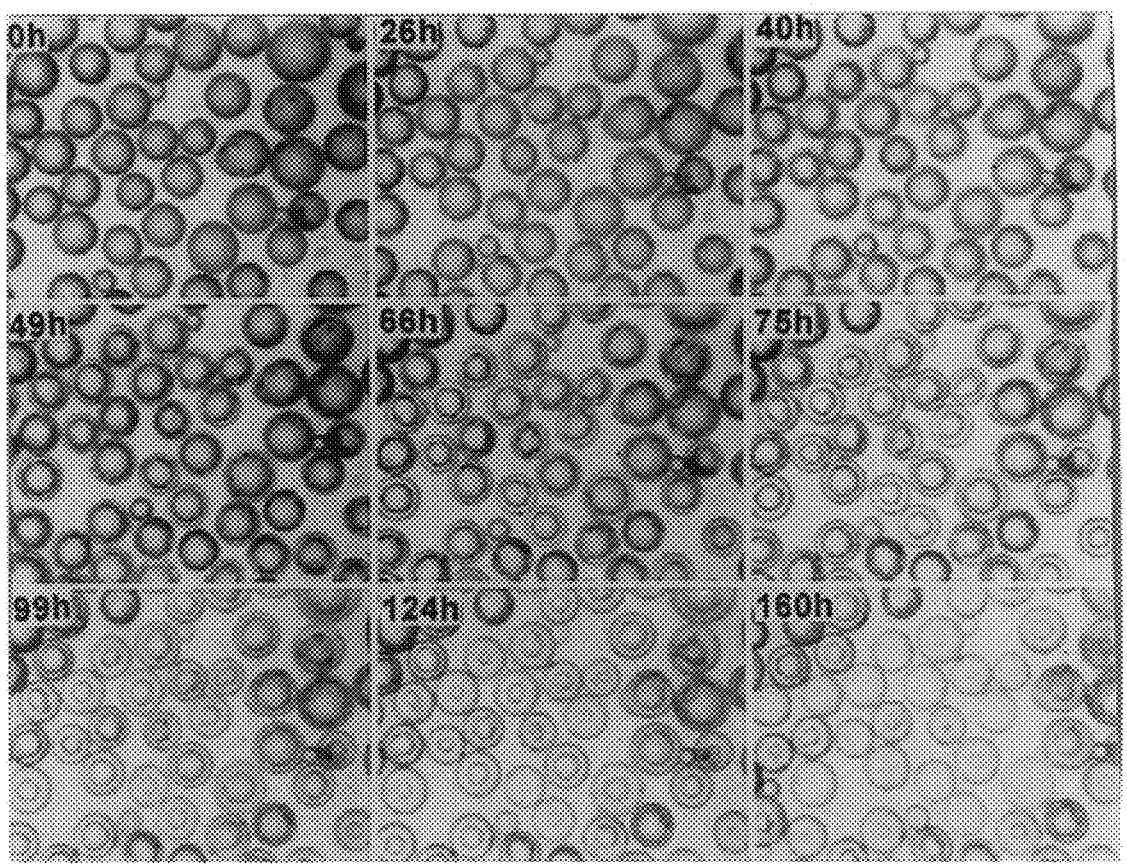
FIG. 5 shows chronological video images (220×) of a group of DyLAB-10 glass microspheres after immersion in PBS solution (pH 7.4) at 22° C. for the time (in hours) shown in the upper left corner. The layer forming on the outer surface of the glass microspheres becomes detectable after about 26 hours and becomes progressively thicker with time. The external diameter of the microspheres remains nearly constant while the diameter of the unreacted core becomes progressively smaller. The average diameter of the microspheres was 28 μm.

Degradation of the rare earth lithium borate glass materials of the invention was observed during in vitro testing as set forth hereinafter. The DyLAB glass microspheres shown in FIG. 5 demonstrate the unique degradation characteristics of the glass materials of the invention. Although none of the radioactive component is released, the glass material began to react within 24 hours in a PBS solution at 37° C. This is shown in FIG. 5 as the formation of a rare earth rich reaction layer on the DyLAB microspheres and indicates that the glasses will be degradable in the body.

The degradation rate of the glass materials of the invention can be easily controlled from approximately $10^{-6}$ to $10^{-10}$ g/cm$^2$/min. by adjusting the glass composition. Thus, the rare earth-lithium borate glasses of the invention can safely accommodate a variety of useful radioisotopes (beta or gamma emitters) whose half-life ranges from as little as 2 hours to as much as 7 days. This factor greatly enhances the versatility of the glass materials of the invention for in vivo radiotherapy.

Figure 6:
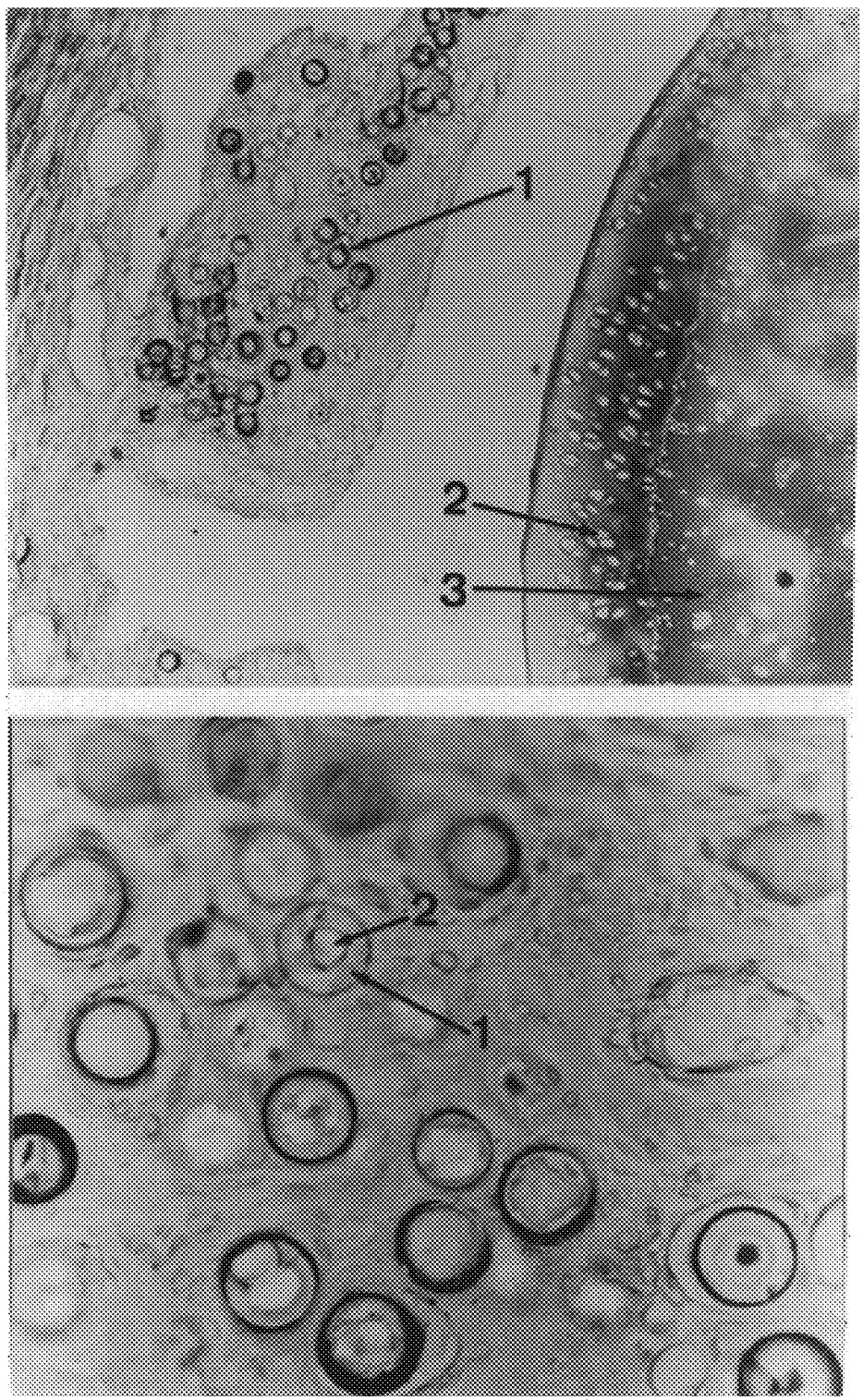
FIG. 6 shows photomicrographs (A) 120× and (B) 480× of DyLAB-10 glass microspheres (20–25 μm in diameter) imbedded in a synovial membrane two weeks after injection into the healthy stifle joint of a rat. The arrows in (A) point to (1) the glass microspheres imbedded in the synovial membrane; (2) the articular cartilage and (3) bone. Degradation of the glass microspheres is indicated in (B); a corrosion layer (1) surrounds a glass core (2)
Figure 7:
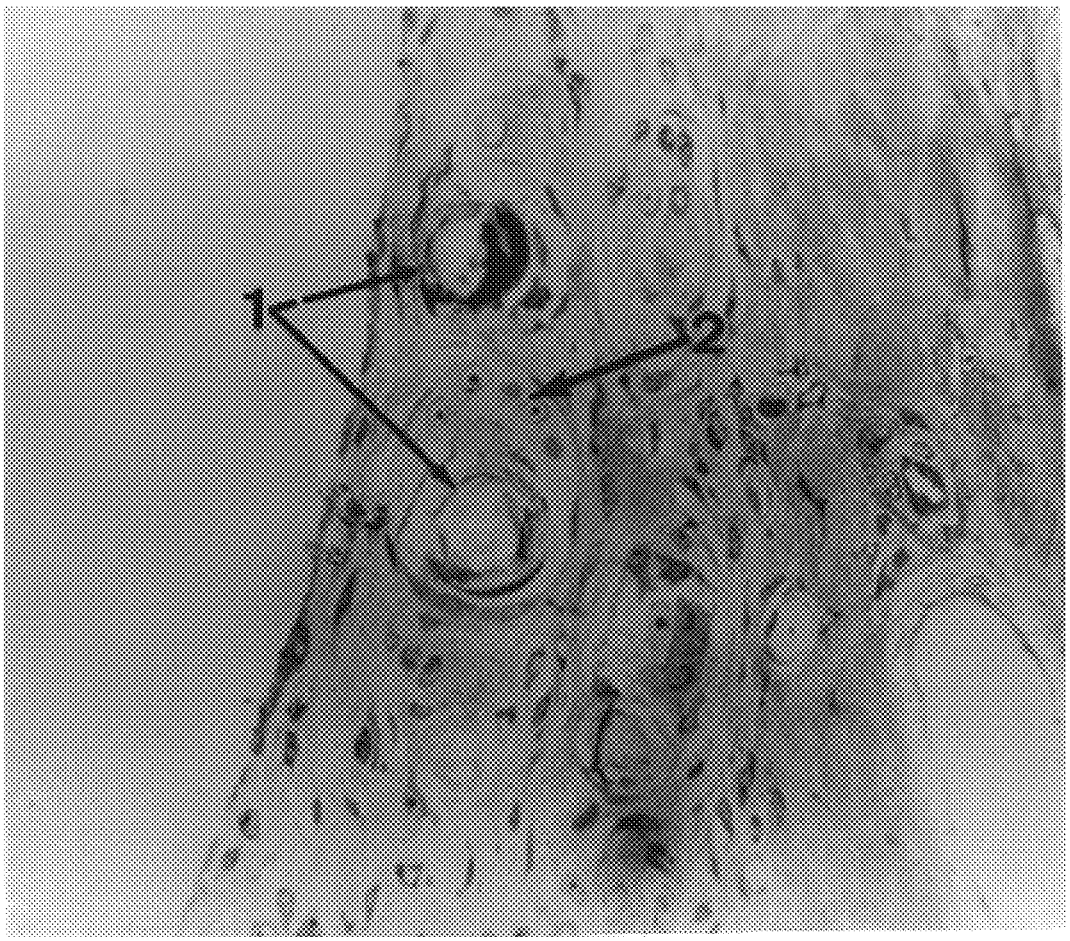
FIG. 7 is a photomicrograph (480×) of (1) two DyLAB-10 glass microspheres engulfed by (2) macrophages (elliptical shape) two weeks after injection into the healthy stifle joint of a rat. Degradation of the microspheres is indicated by discoloration at the surface and by a change in shape from spherical to irregular.

The results of the in vitro studies and in vivo testing of the glass materials of the invention set forth hereinafter are in good agreement. A reaction or corrosion layer, similar to that shown in FIG. 5, also formed on the glass microspheres that were injected into the healthy stifle joints of a rat (see FIGS. 6 and 7). There was no detected difference between the dissolution characteristics of the glass microspheres injected into the joints of a rat and those immersed in simulated body fluids.

The glass materials of the present invention, in the form of microspheres, may be prepared from a homogeneous mixture of powders (i.e. the batch) that is melted to form the desired glass composition. The exact chemical compounds or raw materials used for the batch is not critical so long as they provide the necessary oxides in the correct proportion for the melt composition being prepared. The mole and weight percent of illustrative components of glass materials of the invention are set forth in Tables II through V hereinafter. The purity of each raw material is typically greater than 99.9%. After either dry or wet mixing of the powders to achieve a homogeneous mixture, the mixture may be placed in a platinum or platinum/rhodium alloy crucible for melting in an electric furnace. The raw materials must not contain impurities that become radioactive from neutron irradiation.

After the crucible is removed from the furnace, the melt is then cast into a bar or patty on a stainless steel plate. For glass microsphere formation, the glasses are crushed with a mortar and pestle to obtain glass powders. The powders are then fed to a propane/air flame where each particle is melted and spheroidized due to surface tension. The spherical particles are cooled to solid glass microspheres and collected. The glass materials of the invention can be readily made into microspheres of nearly any desired size, preferably having a diameter of less than approximately 100 microns and, more preferably, a diameter between approximately 1 and 40 microns.

The glass materials of the invention, in particulate form such as microspheres, may be activated by being subjected to an effective amount of neutron irradiation which will produce a beta or gamma radiation emitting radioisotope such as, for example, dysprosium-165, holmium-166, yttrium-90, rhenium-186, rhenium-188 or samarium-153, the amount depending upon the particular isotope of such elements that has been chemically dissolved and uniformly distributed throughout the glass materials. Since the glass materials are made radioactive after they are fabricated, all glass melting and fabrication into microspheres, for example, advantageously involves only non-radioactive materials.

As indicated, the radioactive glass compositions of the present invention prepared as described may be administered for the in vivo irradiation of diseased organs such as malignant tumors and the inflamed synovium of arthritic joints. These novel glass compositions in the form of glass microspheres, for example, may be administered by intra-articular injection or by other suitable means of administration. When employed for radiation synovectomy of arthritic joints, for example, the glass compositions are introduced into synovial fluid, become distributed reasonably uniformly in the synovial membrane to a depth of about 50 to 100 microns, and emit beta radiation to substantially fully irradiate the thickness of the membrane without significant dosage to more distant joint structures with the radioisotope being retained in the glass material to prevent migration from the treatment site.

The novel glass compositions of the present invention offer the significant advantages of in situ degradability, significantly decreased potential for radiation escaping from the treatment site, and ease of preparation. Such glass compositions also enable the use of larger radiation doses than can currently be delivered by non-glass radiotherapy materials, use relatively inexpensive materials and can be delivered to essentially any site in the body by simple injection. The nonradioactive glass compositions of the invention also possess an indefinite shelf life.

The following examples illustrate the practice of the invention.

EXAMPLE 1

(1) Glass Preparation

The rare earth-lithium borate glasses listed in Table I, containing either $Dy_2O_3$, $Ho_2O_3$, $Y_2O_3$ or $Sm_2O_3$, were prepared by melting a homogeneous mixture of analytical grade powders of the rare earth oxides in a platinum or platinum/rhodium alloy crucible in an electric furnace. All bath materials used in glass preparation were oxides with the exception of $H_3BO_3$ and $Li_2CO_3$.

TABLE I

Mole Percent Composition of Rare Earth-Lithium-Borate Glasses Investigated for Use as a Biodegradable Radiopharmaceutical.

| Glass Series | X $(RE_2O_3)$* (mole %) | Y (mole %) |
|---|---|---|
| DyLB | | |
| $xDy_2O_3.(100 - x)LiB_3O_5$ | 0.8–3.9 | |
| $xDy_2O_3.yLi_2O.(100 - x - y)B_2O_3$ | 1.9–1.3 | 12.8–59.2 |
| DyMLB | | |
| $xDy_2O_3.yMgO.(100 - x - y)LiB_3O_5$ | 1.7–3.8 | 1.6–24.5 |
| $xDy_2O_3.yMgO.(100 - x - y)Li_2B_8O_{13}$ | 3.9 | 9.0, 3.6 |
| DyLAB | | |
| $5Dy_2O_3.3MgO.5SiO_2.yAl_2O_3.(87 - y)Li_2B_8O_{13}$ | 5.0 | 5–20 |

TABLE I-continued

Mole Percent Composition of Rare Earth-Lithium-Borate Glasses Investigated for Use as a Biodegradable Radiopharmaceutical.

| Glass Series | X $(RE_2O_3)$* (mole %) | Y (mole %) |
|---|---|---|
| HoLB | | |
| $0.5Ho_2O_3.yLi_2O.(100 - y)B_2O_3$ | 0.5 | 4.7–41.0 |
| HoLAB | | |
| $2Ho_2O_3.3MgO.5SiO_2.yAl_2O_3.(90 - y)Li_2B_8O_{13}$ | 2.0 | 5–20 |
| YLAB | | |
| $5Y_2O_3.3MgO.5SiO_2.10Al_2O_3.77Li_2B_8O_{13}$ | 5.0 | — |
| SmLAB | | |
| $5Sm_2O_3.3MgO.5SiO_2.10Al_2O_3.77Li_2B_8O_{13}$ | 5.0 | — |

*RE = Dy, Ho, Y, or Sm.

Most of the glasses were melted between 1000 and 1150° C. The melting temperature of the glasses which contained both $Al_2O_3$ and $SiO_2$ was slightly higher at 1200 to 1300° C. Each melt was held at its melting temperature for approximately 30 minutes (up to one hour for the RELAB glasses) to assure complete melting and homogeneity. After this period, the melts were stirred once with an alumina rod and cast into a bar or patty on a stainless steel plate.

The glasses were stored in a desiccator until they were annealed for property measurements or crushed for spheroidization. The batch composition of the rare earth-lithium borate glasses are listed in Tables II through V.

TABLE II

Mole and Weight % Composition (wt % in Parenthesis) of DyLB Glasses.

| Glass | $B_2O_3$ | $Li_2O$ | $Dy_2O_3$ | $Li_2O/B_2O_3$ | Glass Formation* |
|---|---|---|---|---|---|
| DyLB-1 | 74.37 (83.11) | 24.79 (11.89) | 0.84 (5.00) | 0.33 | H. Glass (P) |
| DyLB-2 | 74.04 (80.93) | 24.68 (11.58) | 1.28 (7.49) | 0.33 | H. Glass (P) |
| DyLB-3 | 73.68 (78.73) | 24.57 (11.27) | 1.75 (10.00) | 0.33 | H. Glass (P) |
| DyLB-4 | 72.90 (74.33) | 24.36 (10.66) | 2.75 (15.01) | 0.33 | H. Glass (P) |
| DyLB-5 | 72.04 (69.92) | 24.10 (10.04) | 3.85 (20.04) | 0.33 | H. Glass (P) |
| DyLB-6 | 85.26 (84.46) | 12.84 (5.46) | 1.90 (10.08) | 0.15 | H. Glass (P) |
| DyLB-7 | 81.76 (82.76) | 16.62 (7.24) | 1.84 (10.00) | 0.20 | H. Glass (P) |
| DyLB-8 | 78.53 (81.28) | 19.67 (8.74) | 1.80 (9.98) | 0.25 | H. Glass (P) |
| DyLB-9 | 70.17 (76.77) | 28.12 (16.21) | 1.71 (10.02) | 0.40 | H. Glass (P) |
| DyLB-10 | 67.82 (75.43) | 30.50 (14.56) | 1.68 (10.01) | 0.45 | H. Glass (P) |
| DyLB-11 | 59.06 (70.00) | 39.37 (20.03) | 1.57 (9.97) | 0.67 | P. Crystalline (SQ) |
| DyLB-12 | 49.26 (62.96) | 49.28 (27.04) | 1.46 (10.00) | 1.00 | P. Crystalline (SQ) |
| DyLB-13 | 39.46 (54.77) | 59.20 (35.27) | 1.34 (9.96) | 1.50 | P. Crystalline (SQ) |

*(P) = Cast on steel plate; (SQ) = Splat quenched between steel plates; H = Homogeneous; S = Slightly; P = Partly

TABLE III

Mole and Weight % Composition (wt % in Parenthesis) of HoLB Glasses.

| Glass | $B_2O_3$ | $Li_2O$ | $Dy_2O_3$ | $Li_2O/B_2O_3$ | Glass Formation* |
|---|---|---|---|---|---|
| HoLB-1 | 94.80 (95.25) | 4.70 (2.03) | 0.05 (2.73) | 0.05 | H. Glass (P) |
| HoLB-2 | 90.50 (93.23) | 9.00 (3.98) | 0.50 (2.80) | 0.10 | H. Glass (P) |
| HoLB-3 | 82.90 (89.39) | 16.60 (7.68) | 0.50 (2.93) | 0.20 | H. Glass (P) |
| HoLB-4 | 76.50 (85.87) | 23.00 (11.08) | 0.50 (3.05) | 0.30 | H. Glass (SQ) |
| HoLB-5 | 73.70 (84.24) | 25.80 (12.66) | 0.50 (3.10) | 0.35 | S. Crystalline (SQ) |
| HoLB-6 | 71.10 (82.67) | 28.40 (14.17) | 0.50 (3.16) | 0.40 | H. Glass (SQ) |
| HoLB-7 | 68.60 (81.11) | 30.90 (15.68) | 0.50 (3.21) | 0.45 | H. Glass (SQ) |
| HoLB-8 | 66.30 (79.63) | 33.20 (17.11) | 0.50 (3.26) | 0.50 | M. Crystalline (SQ) |
| HoLB-9 | 58.50 (74.23) | 41.00 (22.33) | 0.50 (3.44) | 0.70 | P. Crystalline (SQ) |

*(P) = Cast on steel plate; (SQ) = Splat quenched between steel plates; H = Homogeneous; S = Slightly; P = Partly; M = Mostly

TABLE IV

Mole and Weight % Composition (wt % in Parenthesis) of DyMLB Glasses.

| Glass | $B_2O_3$ | $Li_2O$ | $Dy_2O_3$ | MgO | $Li_2O/B_2O_3$ | Glass Formation* |
|---|---|---|---|---|---|---|
| DyMLB-1 | 73.43 (77.82) | 24.22 (11.17) | 1.74 (10.01) | 1.61 (1.00) | 0.33 | H. Glass (P) |
| DyMLB-2 | 70.69 (69.02) | 23.67 (9.92) | 3.83 (20.04) | 1.80 (1.02) | 0.33 | H. Glass (P) |
| DyMLB-3 | 68.92 (67.85) | 23.03 (9.73) | 3.79 (19.99) | 4.26 (2.43) | 0.33 | H. Glass (P) |
| DyMLB-4 | 65.74 (65.63) | 21.96 (9.41) | 3.74 (20.01) | 8.56 (4.95) | 0.33 | H. Glass (P) |
| DyMLB-5 | 59.65 (61.26) | 19.94 (8.79) | 3.63 (19.97) | 16.78 (9.98) | 0.33 | H. Glass (P) |
| DyMLB-6 | 53.96 (56.91) | 18.00 (8.15) | 3.54 (19.98) | 24.50 (14.96) | 0.33 | H. Glass (P) |
| DyMLB-7 | 70.49 (68.05) | 16.65 (6.90) | 3.87 (20.03) | 8.98 (5.02) | 0.24 | H. Glass (P) |
| DyMLB-8 | 74.75 (70.84) | 17.70 (7.20) | 3.94 (19.98) | 3.61 (1.98) | 0.24 | H. Glass (P) |

* H = Homogeneous; (P) = cast on steel plate.

TABLE V

Mole and Weight % Composition (wt % in Parenthesis) of RELAB Glasses** (RE = Dy, Ho, Y, or Sm).

| Glass | $B_2O_3$ | $Li_2O$ | $RE_2O_3$ | $Al_2O_3$ | MgO | $SiO_2$ | Glass Formation* |
|---|---|---|---|---|---|---|---|
| Dy-LAB-5 | 66 (58.39) | 16 (6.08) | 5 (23.70) | 5 (6.48) | 3 (1.54) | 5 (3.82) | H. Glass (P) |
| Dy-LAB-10 | 62 (53.48) | 15 (5.55) | 5 (23.11) | 10 (12.63) | 3 (1.50) | 5 (3.72) | H. Glass (P) |
| Dy-LAB-15 | 58 (48.81) | 14 (5.06) | 5 (22.55) | 15 (18.49) | 3 (1.46) | 5 (3.63) | H. Glass (P) |
| Dy-LAB-20 | 54 (44.37) | 13 (4.58) | 5 (22.01) | 20 (24.07) | 3 (1.43) | 5 (3.55) | H. Glass (P) |
| Ho- | 68 | 17 | 2 | 5 | 3 | 5 | H. |

TABLE V-continued

Mole and Weight % Composition (wt % in Parenthesis) of RELAB Glasses** (RE = Dy, Ho, Y, or Sm).

| Glass | $B_2O_3$ | $Li_2O$ | $RE_2O_3$ | $Al_2O_3$ | MgO | $SiO_2$ | Glass Formation* |
|---|---|---|---|---|---|---|---|
| LAB-5 | (68.22) | (7.33) | (10.91) | (7.36) | (1.75) | (4.34) | Glass (P) |
| Ho-LAB-10 | 64 (32.49) | 16 (6.71) | 2 (10.60) | 10 (14.30) | 3 (1.70) | 5 (4.21) | H. Glass (P) |
| Ho-LAB-15 | 60 (56.97) | 15 (6.11) | 2 (10.31) | 15 (20.86) | 3 (1.65) | 5 (4.10) | H. Glass (P) |
| Ho-LAB-20 | 56 (51.75) | 14 (5.55) | 2 (10.03) | 20 (27.07) | 3 (1.61) | 5 (3.99) | H. Glass (P) |
| Y-LAB-10 | 66 (58.85) | 16 (6.11) | 5 (15.39) | 10 (13.90) | 3 (1.65) | 5 (4.10) | H. Glass (P) |
| Sm-LAB-10 | 62 (54.30) | 15 (5.64) | 5 (21.94) | 10 (12.83) | 3 (1.52) | 5 (3.78) | H. Glass (P) |

*H = Homogeneous; (P) = cast on steel plate.
**$Li_2O/B_2O_3$ = 0.24 for all RELAB glasses.
†The number included in the glass ID corresponds to the mole % $Al_2O_3$ in the glass (For the RELAB glasses only).

(2) Property Measurements

The density of the glasses at 25° C. was measured by Archimedes' buoyancy method using kerosene as the suspension medium whose density (0.8015 g/cm² at 25° C.) was determined using a Gay-Lussac specific gravity bottle. For density measurement, the dry and suspended mass of a crack-and bubble-free piece of each annealed glass was measured on an analytical balance. The experimental error in the density was estimated to be ±0.01 g/cm².

The $n_D$ refractive index was measured by the Becke line method using certified refractive index liquids and a filter which transmitted only sodium D(589 nm) light. Annealed glasses that were crushed with a porcelain mortar and pestle were used for the refractive index measurement. The error for the refractive index was ±0.002.

(3) Chemical Durability Measurement

The chemical durability of the glasses that contained $Dy_2O_3$ or $Ho_2O_3$ was evaluated by measuring the weight loss of as-cast or annealed bulk glass samples that were immersed in phosphate buffered saline (PBS) solution (pH 7.4) at 37° C. PBS solution at 37° C. was used as the corrosion medium to simulate both the ion content, listed in Table VI, and temperature of body fluids, e.g. synovial fluid.

TABLE VI

Molar Content of Inorganic Electrolytes in Phosphate Buffered Saline (PBS) Solution Used in Corrosion Testing of RELAB Glasses.

| Species | Mole/liter × $10^{-3}$ (mM) |
|---|---|
| $Na^+$ | 153.1 |
| $K^+$ | 4.2 |
| $Cl^-$ | 139.6 |
| $H_2PO_4^-/HPO_4^{2-}$ | 9.6 |

The as-cast samples for corrosion testing were selected from pieces of the DyLB, HoLB, DyMLB, DyLAB or HoLAB glasses that were free of cracks or thin, pointed edges.

Rectangular glass samples (plates) for corrosion testing were cut from annealed DyMLB and DyLAB glasses and polished to a 0.05 μm surface finish using SiC paper and $Al_2O_3$ polishing abrasive. Only non-aqueous lubricants, i.e. kerosene and mineral oil, were used during the cutting and polishing to avoid corrosion of the glass before testing. Any residual kerosene or mineral oil was removed from the glass surface prior to testing by rinsing the plates with acetone. Glass plates (≈10×5×2 mm) were used so that the dissolution rate (DR in g/cm²/min.) could be calculated from the weight loss of the glass. Prior to immersion in the PBS solution, the surface area of the DyMLB and DyLAB glass plates was estimated from their bulk dimensions, and the initial weight of all the glass samples was determined.

The bulk glass samples (as-cast pieces or annealed glass plates) were immersed separately in approximately 100 ml of PBS solution at 37° C. that was contained in high density polyethylene (HDPE) bottles. The glass samples were periodically removed from the PBS solution, gently rinsed with acetone to remove any residual PBS, and dried in air at 70° C. for at least 30 minutes. After drying, the reacted or corroded glass samples were weighed and placed back into their respective PBS solution for further testing. These steps were repeated several times for up to 18 days (or 75 and 90 days for the DyLAB and HoLAB glasses respectively).

Inductively coupled plasma spectroscopy (ICP) was used to measure the amount of Dy, if any, released from the DyLB and DyMLB glass samples after immersion in the PBS solution at 37° C. for 5 or 24 hours. Approximately 10 ml of the PBS solution from each glass sample was decanted and replaced with fresh solution. The decanted PBS solution was filtered to remove any particulates and analyzed by ICP to determine the Dy concentration. Note that within 5 and 24 hours, 77.8 and 99.9% of radioactive $^{165}Dy$, respectively, decays to its non-radioactive daughter, $^{165}Ho$.

(4) Glass Microsphere Preparation

The feasibility of preparing glass microsphere for in vivo use from rare-earth lithium borate glasses was tested using the flame spheroidization technique. Flame spheroidization was attempted using at least one of each of the DyLB, HoLB, DyMLB, DyLAB and HoLAB glass compositions from Table I above. Each glass was crushed with a porcelain mortar and pestle and sieved to obtain a −45 μm (−325 mesh) powder. The glass powder was slowly dropped into a propane/air flame, via a vibrating spatula located above the flame, where each particle became molten and was drawn into a sphere by surface tension. Upon exiting the flame, the spherical droplets cooled to a glass and were collected in a stainless steel cylinder.

RESULTS (1) Rare Earth-Lithium Borate Glass Formation

Each rare earth-lithium borate glass batch completely melted and become bubble-free after being held at its respective melting temperature (1000 to 1300° C.) for a few minutes. All of the glass melts were noticeably more fluid than molten $B_2O_3$ or most glass forming silicate melts. The viscosity of a typical soda-lime-silicate glass at its "melting" temperature, 1450° C., is 10 to 100 poise. The low viscosity of the rare earth-lithium borate glass melts is an advantage since it aids homogenization of the melt and decreases the time needed for fining which limits any loss of the more volatile elements such as boron and lithium. There was no evidence of volatilization from the rare earth-lithium borate melts, except for slight fuming that was only observed for the Dy-LAB-20 melt that was melted at 1300° C.

Most of the DyLB and HoLB and all of the rare earth-lithium borate glasses that contained $Al_2O_3$, MgO and and/or $SiO_2$ (DyMLB, DyLAB, HoLAB, YLAB and SmLAB) formed a clear glass when cast on a steel plate, as indicated in Tables II through VI. The rare earth-lithium borate glasses contained some striae but otherwise appeared homogeneous. All of the rare earths, except Y, resulted in colored glass, orange for Ho and yellow for Dy or Sm.

(2) Density and Refractive Index

The density of the rare earth-lithium borate glasses ranged from 2.29 to 2.95 g/cm$^3$ and increased linearly with increasing mole % $Re_2O_3$.

The refractive index ($n_D$) of the rare earth-lithium borate glasses ranged from 1.544 to 1.604 and increased with increasing mole % rare earth oxide, which was expected from the increase in density. However, fluctuations in the refractive index due to the addition of $Al_2O_3$ or MgO were more pronounced than those for the density of the rare earth-lithium borate glasses.

(3) Chemical Durability to the Rare Earth-Lithium Borate Glasses

The chemical durability of a rare earth-lithium borate glass is important from the standpoint of both unwanted radiation leakage and eventual disintegration and dissolution of the glass. The rare earth-lithium borate glass microspheres should preferably completely retain the rare earth radionuclide within the treatment site while it is still significantly radioactive, which is approximately one, 11, 20 or 27 days (i.e. 10 half-lives) for $^{165}$Dy, $^{166}$Ho, $^{90}$Y, or $^{153}$Sm, respectively. Ten half-lives correspond to the time when 99.9% of the radiation has decayed, at which point the rare earth-lithium borate glass microspheres could completely disintegrate without releasing harmful amounts of radiation.

(a) Release of Dy

No detectable amount of Dy ($\geq$0.1 ppm) was found by ICP analysis in any of the PBS solutions that were in contact with the DyLB (1 through 5) or DyMLB glasses for 5 to 24 hours at 37° C. These results were confirmed by testing two additional samples of each DyMLB glass.

(b) Weight Loss and Dissolution Rate

The chemical durability of the rare earth-lithium borate glasses varied drastically with composition, and generally increased with increasing mole % rare earth oxide. The weight loss and dissolution rate (DR) for the DyLB and DyMLB glasses after 8 days and the DyLAB and HoLAB glasses after 7 days are listed in Tables VII and VIII, respectively.

Overall, the HoLB and DyLB glasses were the least durable rare earth-lithium borate glasses. The DyLB-1 through DyLB-5 glasses, which contained from 0.84 to 3.9 mole % $Dy_2O_3$, respectively, were more durable than the HoLB glasses and did not fully react within 24 hours. As a whole, the DyMLB glasses were slightly more durable than the DyLB glasses and had from 1.0 to 13.7% weight loss after immersion in the PBS solution at 37° C. for 8 days (see Table VII).

TABLE VII

Percent Weight Loss and Dissolution Rate for DyLB, DyALB, and DyMLB Glasses (Mole % $Dy_2O_3$ and $Al_2O_3$ or MgO are included for Comparison.

| Glass | Mole % $Dy_2O_3$ | Mole % $Al_2O_3$ or MgO | % Weight Loss ±0.2%* | DR±₂3 × 10$^{-8}$ (g/cm$^2$/min.)* |
|---|---|---|---|---|
| DyLB-1 | 0.84 | 0 | 24.5 | nm |
| DyLB-2 | 1.28 | 0 | 21.8 | nm |
| DyLB-3 | 1.75 | 0 | 14.3 | nm |
| DyLB-4 | 2.75 | 0 | 7.9 | nm |
| DyLB-5 | 3.85 | 0 | 2.5 | nm |
| DyMLB-1 | 1.77 | 1.61 | 7.9 | nm |
| DyMLB-2 | 3.83 | 1.80 | 3.3 | nm |
| DyMLB-3 | 3.79 | 4.26 | 5.4 | nm |
| DyMLB-4 | 3.74 | 8.56 | 8.1 | 89 |
| DyMLB-5 | 3.63 | 16.78 | 4.4 | 63 |
| DyMLB-6 | 3.54 | 24.50 | 4.8 | 90 |

TABLE VII-continued

Percent Weight Loss and Dissolution Rate for DyLB, DyALB, and DyMLB Glasses (Mole % $Dy_2O_3$ and $Al_2O_3$ or MgO are included for Comparison.

| Glass | Mole % $Dy_2O_3$ | Mole % $Al_2O_3$ or MgO | % Weight Loss ±0.2%* | DR±₂3 × 10$^{-8}$ (g/cm$^2$/min.)* |
|---|---|---|---|---|
| DyMLB-7 | 3.87 | 8.98 | 1.0 | 20 |
| DyMLB-8 | 3.94 | 3.61 | 2.4 | 73 |

*After ≈8 days (200 hours) in PBS solution at 37° C.
(nm) not measured

TABLE VIII

Percent Weight Loss and Dissolution Rate for DyLAB and HoLAB Glasses (Mole % $RE_2O_3$ and $Al_2O_3$ are included for Comparison).

| Glass | Mole % $RE_2O_3$ | Mole % $Al_2O_3$ | % Weight Loss ±0.005%* | DR± 0.1 × 10$^{-8}$ (g/cm$^2$/min.)* |
|---|---|---|---|---|
| DyLAB-5 | 5.0 | 5 | 2.740 | 173.3 |
| DyLAB-10 | 5.0 | 10 | 0.040 | 2.7 |
| DyLAB-15 | 5.0 | 15 | 0.003 | 0.1$^§$ |
| DyLAB-20 | 5.0 | 20 | (nd) | (nd) |
| HoLAB-10 | 2.0 | 10 | 4.866 | 461.0 |
| HoLAB-15 | 2.0 | 15 | 0.822 | 21.2 |
| HoLAB-20 | 2.0 | 20 | (nd) | (nd) |
| YLAB-10 | 5 | 10 | nm | nm |
| SmLAB-10 | 5 | 10 | nm | nm |

†RE = Dy, Ho, Y or Sm
(nm) not measured.
*After ≈7 days in PBS solution 37° C.
$^§$Measured weight loss was within the calculated experimental error.
(nd) No detectable weight loss (±0.05 mg uncertainty).

The DR of the DyMLB glasses (listed in Table VII) was the same order of magnitude (10$^{-7}$ g/cm$^2$ min.) for all the glasses but, like the percent weight loss, was somewhat inconsistent with differences in composition.

The DyLAB glasses were generally much more chemically durable than the DyLB or DyMLB glasses, which was not surprising since the DyLAB glasses had the highest $Dy_2O_3$ content (5 mole %) and contained $SiO_2$, $Al_2O_3$ and MgO. The HoLAB glasses contained less rare earth (2 mole % $Ho_2O_3$) than the DyLAB glasses and were, consequently, less chemically durable. The DyLAB-15, DyLAB-20 and HoLAB-20 glasses, which lost little or no weight in the PBS solution at 37° C. are clearly the least degradable of the rare earth-lithium borate glasses.

(4) Rare Earth-Lithium Borate Glass Microsphere Fabrication

Solid glass microspheres (1 to 40 μm in diameter) were successfully prepared from all of the DyLAB and HoLAB glasses and the DyLB-3, DyLB-8, DyMLB-6, DyMLB-8 and HoLB-5 glasses. The microspheres made from the DyLAB-5 glass exhibited uniformity and smooth surfaces representative of all the rare earth-lithium borate microspheres prepared by flame spheroidization. A small fraction of the rare earth-lithium borate glass microspheres contained one or more small gas bubbles which should not have any adverse effect on the use of the microspheres for radiotherapy.

EXAMPLE 2

(1) Glass Preparation

Fifty grams of each of the dysprosium and holmium glasses listed in the following Table IX were prepared by melting a homogeneous mixture of high purity powders (i.e. $Dy_2O_3$, $H_3BO_3$, $Li_2CO_3$, $Al_2O_3$, $SiO_2$ and Mgo) in a platinum or platinum/rhodium alloy crucible in an electric furnace.

TABLE IX

Mole % Composition of the DyLAB and HoLAB Glasses Investigated for In Vivo Radiotherapy.

| Glass* | $RE_2O_3$** | $Li_2O$ | $Al_2O_3$ | $B_2O_3$ | $SiO_2$ | MgO |
|---|---|---|---|---|---|---|
| DyLAB-5 | 5(23.7) | 16 | 5 | 66 | 5 | 3 |
| DyLAB-10 | 5(23.1) | 15 | 10 | 62 | 5 | 3 |
| DyLAB-15 | 5(22.6) | 14 | 15 | 58 | 5 | 3 |
| DyLAB-20 | 5(22.0) | 13 | 20 | 54 | 5 | 3 |
| HoLAB-10 | 2(10.6) | 16 | 10 | 64 | 5 | 3 |
| HoLAB-15 | 2(10.3) | 15 | 15 | 60 | 5 | 3 |
| HoLAB-20 | 2(10.0) | 14 | 20 | 56 | 5 | 3 |

*The number in each Glass ID corresponds to the mole % $Al_2O_3$ in the glass.
**$Dy_2O_3$ (DyLAB) or $Ho_2O_3$ (HoLAB). Weight % in parenthesis.

All batch materials used to prepare the glasses were oxides except $H_3BO_3$ and $Li_2CO_3$. Each batch melted completely and was mostly bubble free between 1200 and 1300° C. after less than 30 minutes. The viscosity of the melts was much lower than that of soda-lime glass (10 to 100 Poise at ~1500° C.). Each melt was held at its melting temperature for approximately one hour before being stirred with an alumina rod and then cast into a bar or patty on a stainless steel plate. A portion of each dysprosium glass was annealed in air at 500° C. for 30 minutes. The annealed dysprosium glasses were inspected for any residual stress by viewing them through cross polarized light.

(2) Glass Microsphere Formation

For glass microsphere formation, the glasses were crushed with a porcelain mortar and pestle and the particles were sieved to obtain a −45 µm (−325 mesh) glass powder. The glass powder was then fed to a propane/air flame where each particle melted and spheroidized due to surface tension. Upon exiting the flame, the spherical particles cooled to solid glass microspheres and were collected in a large stainless steel cylinder (barrel). Microspheres were prepared from each glass listed in Table IX above. After spheroidization, the glass microspheres were dry sieved to size ranges of +38, −38/+32, −32/+25, −25/+20, and −20 µm in diameter and then stored in a desiccator.

(3) Chemical Durability Measurements (A) Weight Loss.

For corrosion testing of bulk dysprosium and holmium glasses, rectangular samples (plates) were cut from the annealed dysprosium glasses, and an as-cast piece of each holmium glass was selected. The dysprosium glass plates were polished to a 0.05 µm finish using SiC paper and $Al_2O_3$ polishing abrasive. Only non-aqueous lubricants were used during cutting and polishing to minimize potential corrosion of the glass before testing. The lubricants were removed from the glass surface by washing the samples in acetone. The weight and surface area of the bulk dysprosium and holmium glass samples were measured prior to corrosion testing. Since the holmium glass samples were not rectangular, their surface area was only an estimate.

The bulk dysprosium and holmium glass samples were corroded separately using phosphate buffered saline (PBS) solution (pH 7.4) at 37° C. in high density polyethylene bottles. The PBS solution (Sigma Chemical Co., St. Louis, Mo.) was used since its pH and inorganic ion content is very close to that of fluids in the body. The glass surface area to solution volume (SA/V) ratio for each glass sample was approximately 0.1 $cm^{-1}$. Periodically, the glass samples were removed from the PBS solution, briefly submerged in acetone to remove any residual PBS, and dried in air at 70° C. for 30 minutes. The glass samples were then weighed and immediately replaced in their respective PBS solution for further testing. These steps were repeated several times for up to 90 days. The dissolution rate (DR in $g/cm^2/min.$) of each dysprosium and holmium glass for a given period was determined by dividing the weight loss by the initial surface area and elapsed dissolution time.

(B) Solution Analysis.

Inductively coupled plasma spectroscopy (ICP) or scintillation counting of leached radioactive $^{165}Dy$ were used in two separate experiments to quantify the amount of $Dy^{3+}$, if any, that dissolved from the above-noted DyLAB glass microspheres during corrosion. For ICP analysis, approximately 70 mg of non-radioactive DyLAB-5, DyLAB-10, DyLAB-15 or DyLAB-20 glass microspheres (28±4 µm average diameter) were corroded in 30 ml of PBS solution at 37° C. (estimated SA/V~1.8 $cm^{-1}$) for 5 or 24 hours. In one case, ICP was used to analyze the PBS solution that had been in contact with DyLAB-10 glass microspheres for 23 days. After submersion for 5 or 24 hours (or 23 days), the glass microspheres were vacuum filtered from the PBS solution and examined by scanning electron microscopy (SEM). Each PBS solution was analyzed by ICP to determine the amount of Dy and other glass components, i.e. B, Al, Si and Mg, in solution. The ICP equipment used had a lower detection limit of 0.1 ppm for Dy, B, Al, Si and Mg.

The radioactivity of deionized (DI) $H_2O$ in which neutron activated DyLAB-10 or DyLAB-20 glass microspheres were immersed at 37° C. (estimated SA/V~$cm^{-1}$) was measured to determine the amount of radioactive $^{165}Dy$ in solution. Approximately every three hours, ½ of each test solution was removed and replaced with an equal volume of fresh DI $H_2O$. The decanted test solution was filtered to eliminate any glass microspheres and then analyzed by counting the 94 KeV gamma emissions of $^{165}Dy$. The radioactivity of the DyLAB glass microspheres was also measured as a control.

(C) Surface Analysis.

Electron dispersion spectroscopy (EDS) and x-ray photoelectron spectroscopy (XPS) were used to determine the surface composition of as-made and corroded DyLAB glass plates. Of most interest was the concentration of Dy in the corroded surface of the DyLAB glasses as compared to the as-made glass. EDS analysis was performed on the same DyLAB-5 glass plate that had been corroded for the weight less measurement. For XPS analysis, a separate set of DyLAB-10 glass plates were corroded in PBS solution at 37° C. for 0, 5, 24 or 336 hours (2 weeks).

(D) In-Vivo Testing of Glass Microspheres.

A preliminary investigation of the in vivo chemical durability and biocompatibility of the glass microspheres was made by injecting non-radioactive DyLAB-10 glass microspheres directly into the healthy stifle joint (knee) of a rat. The DyLAB-10 glass microspheres (20 to 25 µm in diameter) were suspended in a 75 wt. % glycerol-saline solution (0.04 mg of spheres/µl) prior to injection. The glycerol was used to increase the viscosity of the carrier liquid so that the glass microspheres remained suspended for injection. Fifty and 100 µl of the above suspension, i.e. 2 and 4 mg of DyLAB-10 glass microspheres (roughly 50,000 spheres/mg) were injected into the left and right stifle joint, respectively.

The animal was sacrificed two weeks after injection of the glass microspheres and thin tissue sections were prepared from each stifle joint. For preparation of the tissue sections, the joints were removed from the rat, dehydrated, and fixed in polymethylmethacrylate. Thin sections were cut from the fixed joints, along the sagittal plane, and polished using SiC paper and $Al_2O_3$ polishing abrasive. The polished sections were examined by optical microscopy to determine the physical condition of the DyLAB-10 glass microspheres and the surrounding synovial tissue and any evidence of tissue necrosis or other adverse responses.

RESULTS (1) Rare Earth Glass Formation

All of the dysprosium and holmium melts cooled to a clear glass that was free of bubbles and unmelted batch material. The dysprosium and holmium glasses were yellow or orange in color, respectively, and contained some striae, but were otherwise homogeneous in appearance. Residual stress in the dysprosium glasses was adequately removed by annealing the glasses at 500° C. in air for 30 minutes.

Figure 2:
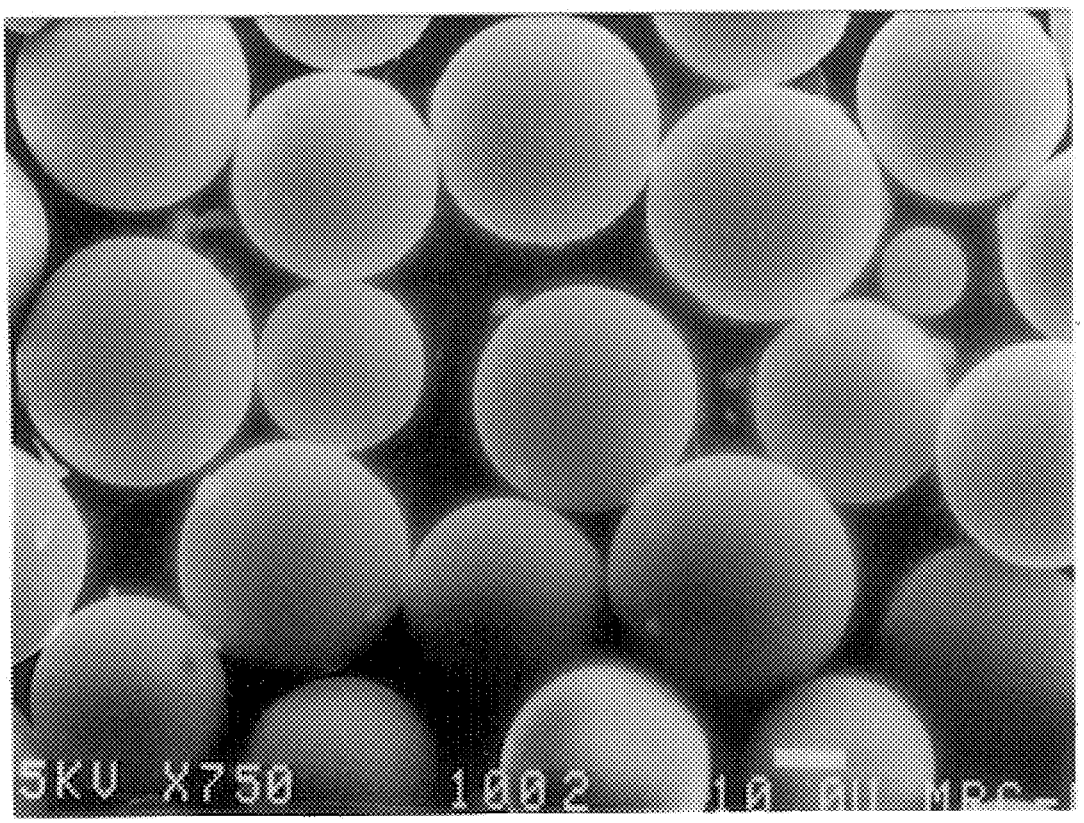
FIG. 2 is a representative SEM photomicrograph of dysprosium-lithium-aluminoborate (DyLAB) glass microspheres prepared by flame spheroidization. White bar is 10 μm.

Microspheres were successfully produced from each of the dysprosium and holmium glasses, and all were alike in both their formation qualities and appearance. The representative photomicrograph in FIG. 2 shows the uniformity and smooth surface texture of the glass microspheres that were prepared by flame spheroidization. Although not visible in FIG. 2, a small fraction of the glass microspheres contained one or more gas bubbles.

(2) Dissolution Rate of Dysprosium and Holmium Glasses

The cumulative percent weight loss per surface area (%WL/cm$^2$) of the bulk dysprosium (5 mole % $Dy_2O_3$) and holmium (2 mole % $Ho_2O_3$) glass samples after immersion in PBS solution at 37° C. for 1, 7 or 75 days (90 days for holmium glasses is listed below in Table X.

TABLE X

Percent Weight Loss Per Surface Area for DyLAB and
HoLAB Glasses Corroded in PBS Solution at 37° C. (SA/V = 0.1 cm$^{-1}$).

| Glass ID | % WL/cm$^2$ ± 0.001 | | |
|---|---|---|---|
| | 24 h | 7 d | 75 d |
| DyLAB-5 | 0.035 | 0.258 | 1.163 |
| DyLAB-10 | 0.007 | 0.009 | 0.166 |
| DyLAB-15 | ** | 0.001† | ** |
| DyLAB-20 | ** | ** | ** |
| | 24 h$^§$ | 7 d$^§$ | 90 d$^§$ |
| HoLAB-10 | ** | 4.443 | 33.532 |
| HoLAB-15 | ** | 0.204 | 2.200 |
| HoLAB-20 | ** | ** | 0.189 |

** -No detectable weight loss (±0.05 mg uncertainty).
†-Measured weight loss within calculated experimental error.
$^§$-Calculated from estimated surface area.

The weight loss results show that the chemical durability of the glasses varied significantly, increasing with increasing $Al_2O_3$ (5 to 20 mole %). For instance, the DyLAB-5 and DyLAB-10 glass plates (5 and 10 mole % $Al_2O_3$, respectively) had a total weight loss of 1.16 and 0.17%/cm$^2$ after 75 days, respectively, whereas the DyLAB-15 and DyLAB-20 glass plates (15 and 20 mole % $Al_2O_3$, respectively) had little to no measurable weight loss. Likewise, the weight loss of the HoLAB glass plates after 90 days decreased from 33.53 to 0.19%/cm$^2$ as the $Al_2O_3$ content increased from 10 to 20 mole %.

The DyLAB glasses were clearly more chemically durable than the HoLAB glasses that contained equal mole % $Al_2O_3$, which is attributed to the difference in the amount (5 or 2 mole % $Dy_2O_3$ or $Ho_2O_3$, respectively) rather than to the specific rare earth oxide. The mole % $Dy_2O_3$ or $Ho_2O_3$ was held constant within each RELAB glass series, DyLAB or HoLAB, in order to standardize the neutron activation time and the resulting specific activity of the RELAB glass microspheres. The chemical durability of the DyLAB and HoLAB glasses was controlled by adjusting the $Al_2O_3$ content which would have no effect on the neutron activation time.

(3) Release of Dysprosium from DyLAB Glass Microspheres

No measurable amount of radioactivity (sub-nCi detection limit) was released from neutron activated DyLAB-10 or DyLAB-20 glass microspheres immersed in deionized water at 37° C. for up to 11 hours (i.e. 4.8 half-lives for $^{165}$Dy during which 96.4% of the radiation decays). The absence of any detectable radiation in the deionized water is important evidence that no radiation would be released outside the treatment site and supports the safety of using DyLAB glass microspheres in vivo. Furthermore, these results demonstrate that neutron activation does not adversely affect the chemical durability of the DyLAB glass microspheres. The lack of Dy release from the radioactive DyLAB glass microspheres was confirmed by similar measurements using nonradioactive microspheres.

The ICP analysis of the PBS solution that was in contact with the DyLAB glass microspheres at 37° C. indicates that the weight loss of the glass was due to dissolution of the non-activatable glass components and not to the dissolution of Dy. No measurable amount of Dy (>0.1 ppm) was detected by ICP analysis of the PBS solution that had been in contact with DyLAB-5, DyLAB-10, DyLAB-15 or DyLAB-20 glass microspheres at 37° C. for up to 24 hours. This is significant since in 24 hours, 99.9% of the $^{165}$Dy decays to its non-radioactive daughter isotope $^{165}$Ho. In other words, no detectable amount of radioactive $^{165}$Dy would be released in the first 24 hours. Dysprosium was likewise not detected in the PBS solution that contained DyLAB-10 glass microspheres for 23 days.

Although there was no evidence that any Dy was dissolved from the DyLAB glass microspheres, detectable amounts of B, Al, Si and Mg were dissolved from the microspheres of each DyLAB glass. The amount of specific glass components that dissolved from the DyLAB glass microspheres decreased with increasing mole % $Al_2O_3$ in the glass, i.e. the overall corrosion resistance of the DyLAB glass microspheres increased with increasing $Al_2O_3$ content, which was also true for the bulk DyLAB glass plates (see Table X).

As has been shown, the RELAB glasses do not dissolve uniformly and none of the radioactive rare earth, including $^{166}$Ho, $^{90}$Y or $^{153}$Sm, would be expected to be released from RELAB glass microspheres. Non-uniform dissolution of the RELAB glass microspheres where the rare earth radionuclide is retained in the glass is clearly an advantage for safe in vivo radiotherepy, especially for glasses that contain the longer-lived $^{166}$Ho, $^{90}$Y or $^{153}$Sm.

(4) Formation of a Dy Rich Reaction Layer

Several techniques were used to verify the formation of a Dy rich reaction layer on the surface of the DyLAB glass plates and microspheres that were immersed in PBS at 37° C.

(A) SEM and Optical Microscopy

Figure 3:
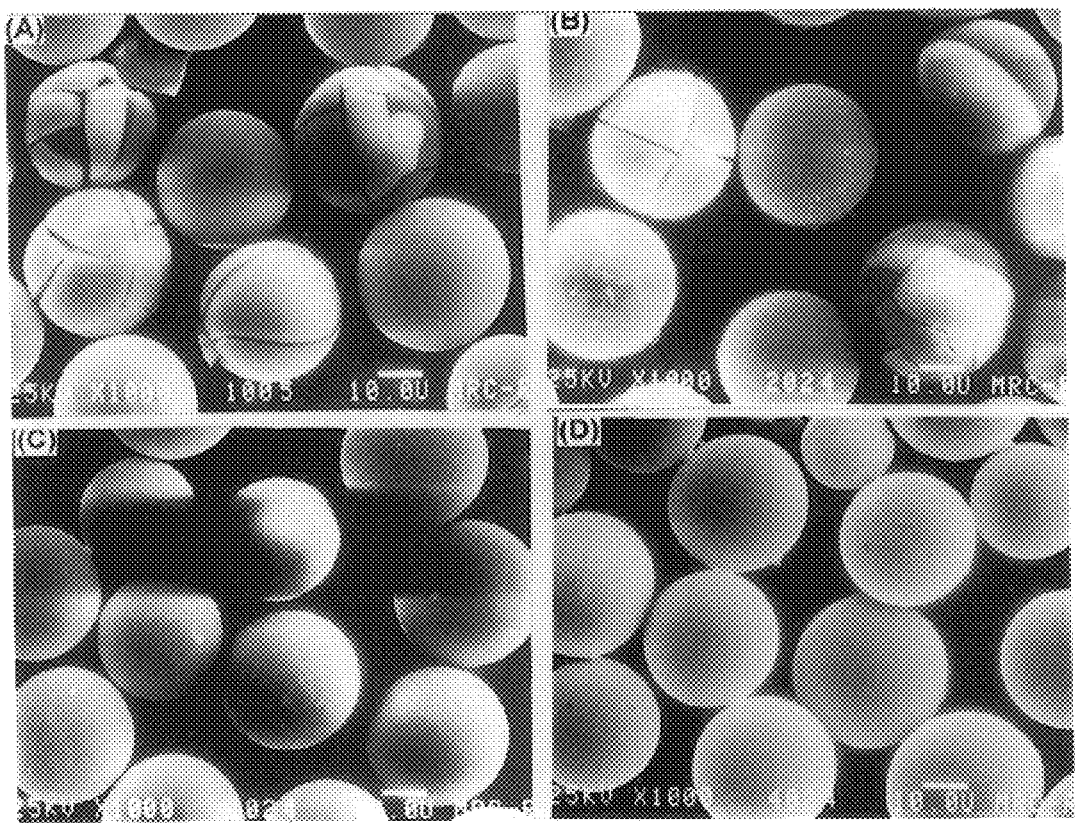
FIG. 3 shows representative SEM photomicrographs of (A) DyLAB-5, (B) DyLAB-10, (C)DyLAB-15, and (D) DyLAB-20 glass microspheres after immersion in PBS solution (pH 7.4) at 37° C. for 24 hours. Shrinkage and cracking on the surface of the DyLAB glass microspheres in both (A) and (B) appeared after the spheres were removed from solution. Notice the smooth surface texture of both the glass and corrosion layer. White bar is 10 μm.

SEM and optical microscopy show that a visible reaction layer formed on both the microspheres and plates of DyLAB-5 and DyLAB-10 glass that were immersed in PBS solution. SEM photomicrographs of the DyLAB-5 and DyLAB-10 glass microspheres after 24 hours in PBS at 37° C. (FIGS. 3(a) and 3(b)) show cracking and partial separation of a layer from the microsphere surface. The cracks on the surface of the DyLAB glass microspheres appeared when the spheres were dried, which suggest capillary stress gradients and shrinkage that are characteristic of dehydration. This indicates that the corroded surface of the DyLAB-5 or DyLAB-10 glass was permeable to the PBS solution and mechanically weaker than the starting glass, probably due to a more open structure and porosity resulting from corrosion.

(B) EDS Analysis

Figure 4:
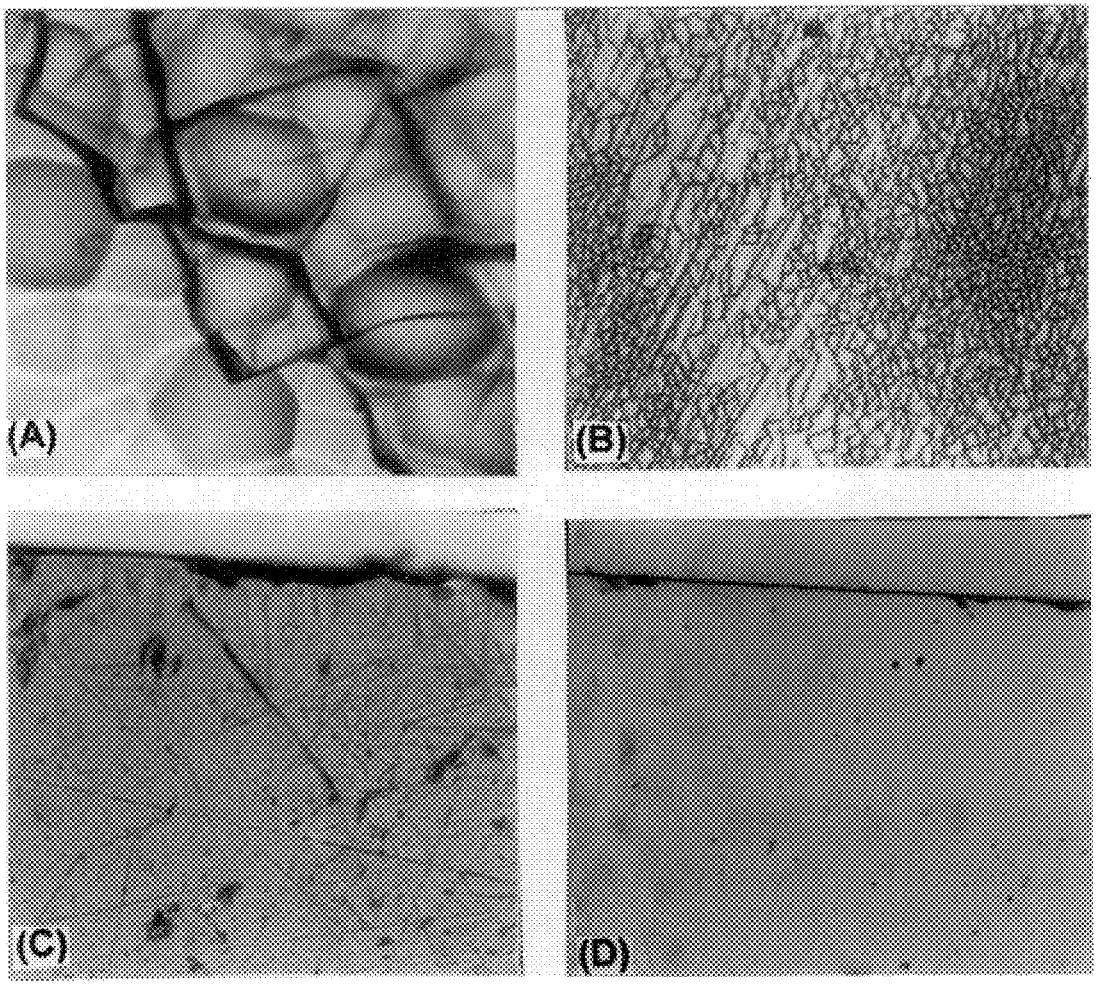
FIG. 4 shows representative photomicrographs (200×) of the surface of a (A) DyLAB-5, (B) DyLAB-10, (C) DyLAB-15, and (D) DyLAB-20 glass plate after immersion in PBS solution (pH 7.4) for 11 days at 37° C. Evidence of a corrosion (reaction) layer is seen (as cracks) in (A) and (B) but not in (C) or (D). The edge of the DyLAB glass plate is shown near the top of the photo in (C) and (D).

Cracks were also seen on the surface of the DyLAB-5 and DyLAB-10 glass plates, pictured in FIGS. 4(*a*) and (*b*). FIG. 4*a* also shows that a fraction of the corrosion layer on the DyLAB-5 glass plate was separated from the glass that had been immersed in PBS at 37° C. for 11 days. From ICP analysis of the solution, it was not surprising that the atomic ratio of Dy to Al plus Si (Dy/Al+Si)), as determined by EDS, was 3.3 times greater in the corrosion layer that separated from the DyLAB-5 glass than in the as-made DyLAB-5 glass. Since no detectable amount of Dy leached from the DyLAB glasses, the concentration of Dy in the corroded glass was expected to increase as the other glass components dissolve in either PBS solution or deionized water. EDS analysis also revealed that Mg, a component of the DyLAB glasses, was absent from the corroded layer on the DyLAB-5 glass.

(C) XPS Analysis

The surface resolution of XPS analysis of glass is 10 to 20 Å, compared to approximately one micron for EDS, and can be combined with ion sputter milling to give a compositional depth profile. The increasing size of the peak caused by Dy in the XPS spectra (not shown) indicates that the concentration of Dy in the DyLAB-10 glass increased as corrosion progressed. Based on the size of the XPS peaks for B and Al, the concentration of B and Al appears lower to a depth of 1000 and 80 Å, respectively, in the DyLAB-10 glass immersed for 5 or 24 hours. The XPS peaks for B and Al in the 2 week DyLAB-10 glass sample most closely resemble those of as-made DyLAB-10 glass plate. The Dy concentration appears to remain the same or to increase in the DyLAB-10 glass even after 2 weeks of corrosion, rather than decrease as it would if Dy was being dissolved from the glass.

XPS analysis also revealed that phosphorus ions from the PBS solution were present in the surface of the DyLAB-10 glass after immersion for 5, 24 or 336 hours. The XPS spectra for the samples immersed for 5 or 24 hours show that the concentration of phosphorus decreased with depth but increased with dissolution time. This concentration gradient suggests that phosphorus was diffusing into the corrosion layer and possibly reacting with the undissolved glass components rather than simply precipitating on the surface.

(D) Real Time Video Microscopy (RTVM)

Reaction of the DyLAB glass microspheres is most vividly shown by real time video microscopy (RTVM). RTVM clearly demonstrates that the size of the DyLAB glass microspheres does not decrease when the microspheres begin to degrade in the PBS solution. The chronological RTVM images in FIG. 5 of the DyLAB-10 glass microspheres in PBS solution (estimated SA/V<0.1 cm$^{-1}$) at 22° C. illustrate the growth of a layer that starts at the outer surface of the microsphere and grows inward with increasing time. This "shell" was first noticed after approximately 5 and 26 hours for the DyLAB-5 and DyLAB-10 glass microspheres, respectively, and is visual proof that a reaction layer was formed on the glass. The images in FIG. 5 show that the outer diameter (reaction layer/solution interface) of the DyLAB-10 glass microspheres remained nearly constant and the reaction layer grew thicker as the glass/corrosion layer interface moved toward the center of each sphere. This gave the appearance of a shrinking, spherical "core" within the DyLAB glass microspheres, which is believed to consist of the unreacted glass. The fact that the outer diameter of the DyLAB glass microspheres did not change is a further indication that the corrosion layer mostly consisted of undissolved glass components rather than reprecipitated compounds.

(5) In Vivo Corrosion of DyLAB Glass Microspheres

A corrosion layer also formed on the surface of non-radioactive DyLAB-10 glass microspheres (23 μm in average diameter) that were injected into the healthy stifle joint (knee) of a rat. Photomicrographs of the DyLAB-10 glass microspheres imbedded in the synovial membrane, FIGS. 6(*a*) and (*b*) (two weeks after injection), show evidence of a corrosion layer, which is similar in appearance to the corroded layer seen on the DyLAB-5 or DyLAB-10 glass microspheres immersed in PBS solution at 22 or 37° C. Likewise, the size of the DyLAB-10 glass microspheres injected into the rat did not decrease noticeably during two weeks in the stifle joint. None of the microspheres were found outside the synovial membrane (see FIG. 6(A)). There was no discernable difference in the stifle joints injected with either 2 or 4 mg of DyLAB-10 glass microspheres.

These results indicate that the corrosion testing in simulated body conditions is representative of the behavior of ReLAB glass microspheres during in vivo use. There is little reason to believe that the corrosion layer on the surface of the DyLAB-10 glass microspheres injected into the rat was appreciably different in composition than that which formed on the surface of the DyLAB-5 or DyLAB-10 glass microspheres immersed in deionized water or PBS solution. Thus, the corrosion layer that forms on DyLAB glass microspheres imbedded in the synovial membrane would be expected to retain most, if not all, of the Dy from the starting glass for at least two weeks after the spheres are injected, at which time all of the microspheres are non-radioactive. This suggests that none of the injected radioactivity from DyLAB or HoLAB glass microspheres would escape, either in the form of glass particulates or dissolved $^{165}$Dy or $^{166}$Ho, outside a human joint during radiation synovectomy.

Equally important is the fact that none of the injected DyLAB-10 glass microspheres (≈100,000 or 200,000 spheres/joint) were found outside the synovial sac. All of the DyLAB-10 glass microspheres appeared to be imbedded in the synovial membrane. This is a critical observation since ReLAB glass microspheres can deliver a more uniform dose of therapeutic radiation when located inside the synovial membrane.

The rat resumed normal activity immediately after the glass microspheres were injected and did not show any negative response during the two weeks the microspheres were in the stifle joints. There was no evidence of necrosis of the joint tissue or physical damage to the articular cartilage, shown in FIG. 6(*a*), one of the five criteria for in vivo use of the RELAB glasses. A foreign body response was observed, and the DyLAB-10 glass microspheres were engulfed by macrophages (phagocytes) which appear as an elliptical halo surrounding the microspheres. The macrophages are visible in FIGS. 6(*a*) and (*b*), but are most clearly shown surrounding the DyLAB-10 glass microspheres pictured on FIG. 7. There was no evidence that the foreign body response observed in the rat caused any harm to the joint, and engulfment of the RELAB glass microspheres by macrophages may be beneficial, since it is considered one method whereby the glass microspheres can be removed from the body when they are no longer radioactive.

In view of the above, it will be seen that the several objects of the invention are achieved and other advantageous results attained.

As various changes could be made in the above compositions and methods without departing from the scope of the invention, it is intended that all matter contained in the above description or shown in the accompanying drawings shall be interpreted as illustrative and not in a limiting sense.

What is claimed is:

1. A nonradioactive glass in particulate form adapted for radiation therapy in a mammal comprising a biodegradable rare earth-lithium borate glass material having a composition selected from the group consisting of:

$$xRE_2O_3.(100-x)LiB_3O_5$$

$$xRE_2O_3.yLi_2O.(100-x-y)B_2O_3$$

$$xRE_2O_3.yMgO.(100-x-y)LiB_3O_5$$

$$xRE_2O_3.yMgO.(100-x-y)Li_2B_8O_{13}$$

$$xRE_2O_3.3MgO.5SiO_2.yAl_2O_3.(92-y-x)Li_2B_8O_{13}$$

wherein RE is a neutron activatable rare earth element which, upon being subjected to an effective amount of neutron irradiation, will produce a beta or gamma emitting radioisotope, said radioisotope being distributed throughout said glass material, x is the mole percent of $RE_2O_3$ and ranges between approximately 0.5 and 5 and y is the mole percent of $Li_2O$, MgO or $Al_2O_3$ and the balance is a lithium borate material glass; wherein said lithium borate glass is substantially free of lithium-6 and boron-10; and wherein said glass upon being introduced into a body fluid for radiation therapy is adapted to react therewith causing said radioisotope to form an insoluble compound on the surface of said glass material which is retained in said glass material and thereby prevented from escaping from the treatment site.

2. A nonradioactive glass as set forth in claim 1 wherein said beta or gamma emitting radioisotope is selected from the group consisting of dysprosium-165, holmium-166, yttrium-90, rhenium-186, rhenium-188 and samarium-153.

3. A nonradioactive glass as set forth in claim 1 wherein said rare earth-lithium borate glass material has the following composition:

| | |
|---|---|
| $Dy_2O_3$ | 1.7 mole % |
| $Li_2O$ | 24.6 mole % |
| $B_2O_3$ | 73.7 mole %. |

4. A nonradioactive glass as set forth in claim 1 wherein said rare earth-lithium borate glass material has the following composition:

| | |
|---|---|
| $Dy_2O_3$ | 5 mole % |
| $Li_2O$ | 16 mole % |
| $Al_2O_3$ | 5 mole % |
| $B_2O_3$ | 66 mole % |
| $SiO_2$ | 5 mole % |
| MgO | 3 mole %. |

5. A nonradioactive glass as set forth in claim 1 wherein said rare earth-lithium borate glass material has the following composition:

| | |
|---|---|
| $Dy_2O_3$ | 5 mole % |
| $Li_2O$ | 15 mole % |
| $Al_2O_3$ | 10 mole % |
| $B_2O_3$ | 62 mole % |
| $SiO_2$ | 5 mole % |
| MgO | 3 mole %. |

6. A nonradioactive glass as set forth in claim 1 wherein said glass is adapted for radiation synovectomy of arthritic joints in a mammal and said glass is introduced into synovial fluid for radiation synovectomy.

7. A nonradioactive glass as set forth in claim 1 wherein said glass is spherical in shape.

8. A nonradioactive glass as set forth in claim 7 wherein said glass is in the form of microspheres having a diameter less than approximately 100 microns.

9. A nonradioactive glass as set forth in claim 8 wherein said microspheres have a diameter between approximately 1 and 40 microns.

10. A nonradioactive glass as set forth in claim 1 wherein said insoluble compound formed by said radioisotope is a rare earth oxide.

11. A nonradioactive glass as set forth in claim 1 wherein said radioisotope is dysprosium-165.

* * * * *

UNITED STATES PATENT AND TRADEMARK OFFICE
CERTIFICATE OF CORRECTION

PATENT NO. : 6,379,648 B1
DATED : April 30, 2002
INVENTOR(S) : Delbert W. Day et al.

It is certified that error appears in the above-identified patent and that said Letters Patent is hereby corrected as shown below:

Column 21,
Line 20, "$x$RE$_2$O$_3$.(100-$x$) LiB$_3$O$_5$" should read -- $x$RE$_2$O$_3$•(100-$x$) LiB$_3$O$_5$, --.
Line 22, "$x$RE$_2$O$_3$.$y$Li$_2$O.(100-$x$-$y$)B$_2$O$_3$" should read
-- $x$RE$_2$O$_3$•.$y$Li$_2$O•(100-$x$-$y$)B$_2$O$_3$, --
Line 24, "$x$RE$_2$O$_3$.$y$MgO.(100-$x$-$y$)LiB$_3$O$_5$" should read
-- $x$RE$_2$O$_3$•$y$MgO•(100-$x$-$y$)LiB$_3$O$_5$, --.
Line 26, "$x$RE$_2$O$_3$.$y$MgO.(100-$x$-$y$) Li$_2$B$_8$O$_{13}$" should read
-- $x$RE$_2$O$_3$•$y$MgO•(100-$x$-$y$)Li$_2$B$_8$O$_{13}$, and --.
Line 28, "$x$RE$_2$O$_3$.3MgO.5SiO$_2$.$y$Al$_2$O$_3$.(92-$y$-$x$) Li$_2$B$_8$O$_{13}$" should read
-- $x$RE$_2$O$_3$•3MgO•5SiO$_2$•$y$Al$_2$O$_3$•(92-$y$-$x$)Li$_2$B$_8$O$_{13}$ --.

Signed and Sealed this

First Day of October, 2002

Attest:

JAMES E. ROGAN
Attesting Officer Director of the United States Patent and Trademark Office